US008157756B2

(12) United States Patent
Schimek et al.

(10) Patent No.: US 8,157,756 B2
(45) Date of Patent: Apr. 17, 2012

(54) ORTHOSIS

(75) Inventors: Norbert Schimek, Kirchworbis (DE); Helmut Wagner, Duderstadt (DE)

(73) Assignee: Helmut Wagner, Duderstadt (DE)

( * ) Notice: Subject to any disclaimer, the term of this patent is extended or adjusted under 35 U.S.C. 154(b) by 310 days.

(21) Appl. No.: 12/528,731

(22) PCT Filed: Feb. 11, 2008

(86) PCT No.: PCT/DE2008/000258
§ 371 (c)(1),
(2), (4) Date: Aug. 26, 2009

(87) PCT Pub. No.: WO2008/104149
PCT Pub. Date: Sep. 4, 2008

(65) Prior Publication Data
US 2010/0063432 A1    Mar. 11, 2010

(30) Foreign Application Priority Data

Feb. 26, 2007    (DE) .................. 10 2007 009 605

(51) Int. Cl.
*A61F 5/00*    (2006.01)
*E05D 7/00*    (2006.01)
*E05D 7/08*    (2006.01)
(52) U.S. Cl. .............................. 602/26; 16/221; 49/388
(58) Field of Classification Search .................. 602/1, 5, 602/23, 26; 16/221, 366, 334, 368, 369; 49/188, 388, 397
See application file for complete search history.

(56) References Cited

U.S. PATENT DOCUMENTS

| 4,886,054 A | 12/1989 | Castillo et al. |
| 5,535,551 A * | 7/1996 | Falk et al. ....................... 49/324 |
| 6,527,733 B1 * | 3/2003 | Ceriani et al. ................... 602/16 |

FOREIGN PATENT DOCUMENTS

| DE | 3738664 | 5/1989 |
| DE | 4418855 | 12/1995 |
| DE | 29705958 | 4/1997 |
| DE | 19811925 | 10/1999 |
| DE | 102005008340 | 2/2005 |
| EP | 0454186 | 6/1988 |
| EP | 1676549 | 10/2004 |
| WO | WO 97/29717 | 2/1997 |
| WO | WO 2006/078428 | 7/2006 |

* cited by examiner

*Primary Examiner* — Patrica Bianco
*Assistant Examiner* — Tarla Patel
(74) *Attorney, Agent, or Firm* — Whitham Curtis Christofferson & Cook, PC

(57) ABSTRACT

A knee orthodic is provided with two load-bearing joints (12, 14), each joint having a proximal leg (16.1, 16.2) and a distal leg (18.1, 18.2). The knee orthodic, may be adapted more easily to a changing knee width. This is achieved in that the proximal legs (16.1, 16.2) are connected by a proximal joint (24) and the distal joints (18.1, 18.2) are connected by a distal joint, said proximal legs (16.1, 16.2) being connected pivotally and fixably relative to one another in the proximal joint (24) in the form of a rotary joint about a proximal joint pivot axis (P).

19 Claims, 5 Drawing Sheets

ORTHOSIS

BACKGROUND OF THE INVENTION

1. Field of the Invention

The invention relates to an orthosis, in particular a knee orthosis, with two load-bearing joints that each have a proximal panel and a distal panel. In other words, the invention relates to an orthosis principle for different parts of the body.

2. Background Description

Orthoses of this kind are used to protect corresponding ligaments from overload under the effects of internal or external forces in such a way that limited and/or unlimited movements of parts of the body are possible. Knee orthoses are used to protect a knee joint from dorsoventral buckling movements. For this purpose, the knee orthosis is secured to a thigh and lower leg in such a way that the two load-bearing joints are arranged laterally of the knee joint that is to be protected. Buckling loads that occur are taken up by the knee orthosis and led past the knee into the thigh and lower leg. To ensure that buckling forces are reliably led away, the load-bearing joints should bear tightly on the knee joint.

Knee orthoses are generally used after operations on the knee in order to protect the still sensitive ligaments of the operated knee. After knee operations, the tissue in the area of the knee is generally swollen, and the swelling subsides during the healing process. The width of the knee changes in this process, and the distance between the load-bearing joints has to be readjusted in order to continually ensure optimal protection against buckling movements.

To permit fine adjustment of the distance between the load-bearing joints, the knee orthoses are adaptable to a small degree and are used together with spacer elements that are positioned between the load-bearing joints and the knee.

U.S. Pat. No. 4,886,054 and DE 44 18 855 A1 disclose knee orthoses in which the distal panels and the proximal panels can each be secured in such a way as to be transversely displaceable relative to each other by means of a bracing device. A disadvantage lies in the complicated structure of the bracing device which, in addition, is not particularly user-friendly.

DE 37 38 664 A1 discloses a knee orthosis in which the proximal panels are secured on a central tab by means of knobs. To change the distance between the load-bearing joints, the distal panels are secured on other knobs. A disadvantage of this is that the distance cannot be varied in a stepless manner. A further disadvantage is the poor user friendliness.

WO 2006/078428 A2 discloses a knee orthosis with a monolithic joint. A disadvantage of this is that the distance between the two proximal panels cannot be fixed. EP 1 676 549 A1 discloses a load-bearing joint. DE 10 2005 008 340 A1 discloses a spherical joint orthosis in which the proximal panels are secured fixedly on a shell. DE 297 05 958 U1 discloses a knee-joint unloading support in which the proximal panels are secured to a strap-on thigh shell.

SUMMARY OF THE INVENTION

The object of the invention is to propose an orthosis, in particular a knee orthosis, which can be more easily adapted to a changing width of the knee.

The problem addressed by the invention is solved by an orthosis having the features of claim 1.

An advantage of the invention lies in the fact that the distance between the load-bearing joints can be adapted to the width of the knee in a stepless manner. For example, if the swelling of the knee fluctuates during the course of the day, the orthosis can be easily readjusted.

Another advantage is that an orthosis according to the invention can be adapted quickly and simply, which saves time both for the patient and also for medical personnel involved in fitting the orthosis.

An orthosis according to the invention also permits great variation in the distance between the load-bearing joints, such that a smaller number of types is sufficient to cover all existing knee widths. Fewer variants of the orthosis according to the invention therefore have to be kept in stock, which results in savings in terms of storage capacity.

Important components of the orthosis, for example the panels, can also be designed as injection-molded components, which results in rapid and inexpensive production, even in large batch sizes.

In the context of the present invention, the load-bearing joints are understood as those joints of the orthosis that move when the knee is bent or extended.

The proximal joint and/or the distal joint is preferably a rotary joint, in particular a fixable rotary joint. Rotary joints are particularly easy to produce and very stable, and they provide sufficient strength for the orthosis. By means of a fixable rotary joint, the distance between the two load-bearing joints can be adjusted steplessly and can be fixed directly after adjustment. In this way, the orthosis can be adapted particularly quickly and easily to a changing width of the knee.

In a preferred embodiment, the proximal joint pivot axis extends through the proximal joint.

The proximal joint and/or distal joint is particularly preferably a scissor-type rotary joint. A scissor-type rotary joint is to be understood as meaning in particular that the two proximal and distal panels extend beyond the rotary joint. If the distance between the two load-bearing joints decreases, a scissor-type rotary joint then also results in a decrease in the distance between the two sections of the panels that extend beyond the scissor-type rotary joint.

Alternatively, the proximal joint and/or distal joint can be arranged laterally on the respective panels, such that the distance between the sections extending beyond the rotary joint decreases when the distance between the load-bearing joints increases. Of course, it is also possible that only the proximal joint or only the distal joint is designed as a scissor-type rotary joint, while the other one is not.

The rotary joint is preferably pivotable about a rotary joint pivot axis that extends perpendicular to a load-bearing joint pivot axis about which the two load-bearing joints are pivotable. The rotary joint pivot axis then extends in the dorsoventral direction.

In a preferred embodiment, the two distal panels each have a first distal panel part and a second distal panel part and each comprise a distal compensating joint, which distal compensating joints connect the respective panel parts to each other pivotably about a pivot axis that extends parallel to the rotary joint pivot axis. Corresponding compensating joints are particularly preferably also provided in the proximal panels. These compensating joints can be hinge joints, for example. Alternatively, the compensating joints are formed by a tapering of the material of the respective panels. Alternatively or in addition, the compensating joints are formed by areas in which the material has a modulus of elasticity lower than that of the surrounding material. When the proximal panels are pivoted relative to each other at the proximal joint, the distance between the load-bearing joints changes. The compensating joints ensure that the two load-bearing joints pivot further about a pivot axis common to both of them. This relieves the strain on the load-bearing joints.

In a preferred embodiment, the proximal panels, seen from the direction of the respective load-bearing joint, run out behind the proximal joint into a quarter shell, such that both quarter shells form a proximal half shell for securing the orthosis to a limb of the body. If the orthosis is a knee orthosis, the half shell is designed to secure the knee orthosis to a thigh.

Analogously, the distal panels, seen from the direction of the respective load-bearing joint, run out behind the distal joint into a quarter shell, such that both quarter shells form a distal half shell for securing the orthosis to a limb of the body. If, once again, the orthosis is a knee orthosis, the distal half shell serves to secure the knee orthosis to a lower leg.

To permit adjustment to the respective limb of the body, the proximal and/or distal quarter shells are flexible.

According to the invention, an elbow orthosis is also provided with two load-bearing joints that each have a proximal panel and a distal panel. Such elbow orthoses are used to protect an elbow joint against lateral and medial buckling movements. For this purpose, the elbow orthosis is secured to an upper arm and a lower arm in such a way that the two load-bearing joints are arranged on both sides of the elbow joint that is to be protected. Buckling loads that occur are taken up by the elbow orthosis and led past the elbow into the upper arm and lower arm. To ensure that the buckling forces are reliably led away, the load-bearing joints should bear tightly on the elbow joint.

Elbow orthoses are generally used after operations on the elbow in order to protect the still sensitive ligaments of the operated elbow. After elbow operations, the tissue in the area of the elbow is sometimes swollen, and the swelling subsides during the healing process. The width of the elbow changes in this process, and the distance between the load-bearing joints has to be readjusted in order to continually ensure optimal protection against buckling movements.

If the load-bearing joints are designed as spherical joints, compensating joints can then advantageously be omitted. Pads, for example, are in this case secured to the load-bearing joints such that the load-bearing joints are not in direct contact with the patient's knee joint.

BRIEF DESCRIPTION OF THE DRAWINGS

Embodiments of the invention are explained in more detail below with reference to the figures, in which.

DETAILED DESCRIPTION OF A PREFERRED EMBODIMENT OF THE INVENTION

Figure 1:
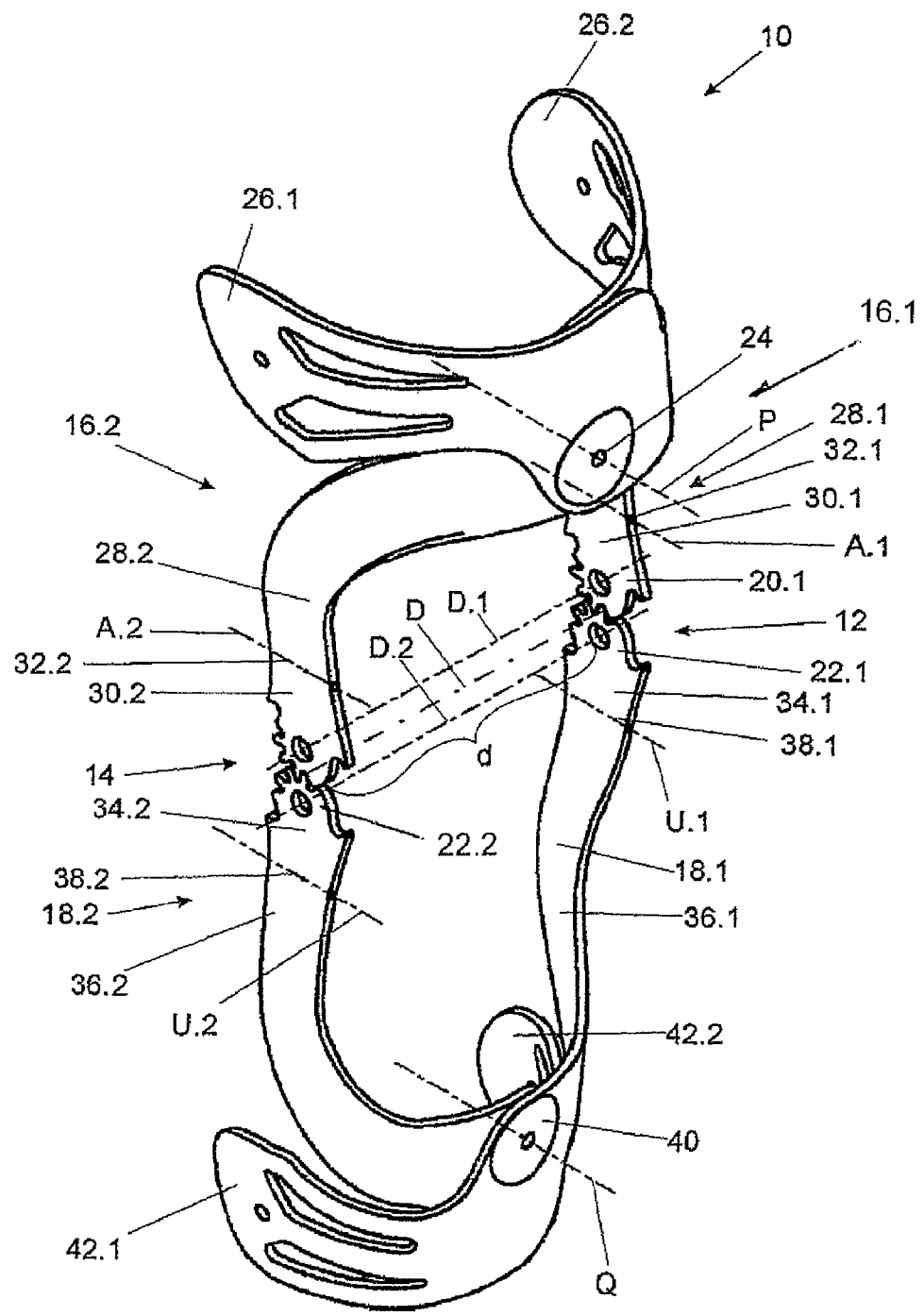
FIG. 1 shows a perspective view of a knee orthosis according to the invention, in which both the proximal joint and also the distal joint are designed as scissor-type rotary joints.

In FIG. 1, a knee orthosis 10 is shown with a left-hand load-bearing joint 12 and a right-hand load-bearing joint 14.

The left-hand load-bearing joint 12 connects a left-hand proximal panel 16.1 to a left-hand distal panel 18.1 and is designed as a polycentric rotary joint. The left-hand load-bearing joint 12 comprises a proximal joint head 20.1 and a distal joint head 22.1, which each have teeth. The teeth mesh with one another when the proximal panel 16.1 pivots relative to the distal panel 18.1. The proximal and distal panels 16.1, 18.1 pivot relative to each other on a time-variable load-bearing joint pivot axis D, which always extends parallel to connecting axes D1 and D2 that connect the midpoints of the two proximal joints heads 20.1, 20.2 of the two distal joint heads 22.1, 22.2. to each other.

The proximal panel 16.1 and the distal panel 18.1 have a flat, strap-like configuration and are produced by injection molding. The knee orthosis 10 additionally comprises a right-hand proximal panel 16.2 and a right-hand distal panel 18.2, which are designed in a substantially mirror-symmetrical manner with respect to the left-hand proximal panel 16.1 and left-hand distal panel 18.1. To avoid repetition, the components of only one side are described below. Each such component with the suffix ".1" has, on the respective other side, a corresponding component with the suffix ".2".

The left-hand proximal panel 16.1 and the right-hand proximal panel 16.2 are connected pivotably at a proximal joint 24 and can be fixed relative to each other, and they can be pivoted relative to each other about a proximal joint pivot axis P. The proximal joint pivot axis P extends perpendicular to the load-bearing joint pivot axis D.

Seen from the direction of the left-hand load-bearing joint 14, the proximal left-hand panel 16.1 extends beyond the proximal joint 24 and runs out into a quarter shell 26.1. In the same way, the right-hand proximal panel 16.2 runs out into a quarter shell 26.2. When the two proximal panels 16.1, 16.2 are pivoted relative to each other such that the distance d between the left-hand loading bearing joint 12 and the right-hand load-bearing joint 14 decreases, the distance between the quarter shells 26.1 and 26.2 also decreases. The proximal joint 24 is therefore a scissor-type rotary joint.

The right-hand proximal panel 16.2 has a first proximal panel part 28.2 and a second proximal panel part 30.2, which are connected to each other via a proximal compensating joint 32.2 and which are pivotable relative to each other about a proximal compensating joint pivot axis A.2.

In the same way, the right-hand distal panel 18.2 has a first distal panel part 34.2 and a second distal panel part 36.2, which are connected to each other via a distal compensating joint 38.2 and which are pivotable relative to each other about a distal compensating joint pivot axis U.2. The distal compensating joint pivot axis U.2. also extends parallel to the proximal joint pivot axis P.

The distal compensating joints 38.1, 38.2 and the proximal compensating joints 32.1 and 32.2 are formed by hinges. In an alternative embodiment, the respective panels 16.1, 16.2 and 18.1, 18.2 have a tapering of the material in the area of the compensating joints 32.1, 32.2 and 38.1, 38.2. According to a further alternative, a material with a lower modulus of elasticity is used in the corresponding area.

The distal panels 18.1 and 18.2 are connected to each other at a distal joint 40 so as to pivot about a distal joint pivot axis Q, and they continue in respective quarter shells 42.1, 42.2. The quarter shells 42.1, 42.2 form a half shell with which the knee orthosis 10 can be secured, for example with bandages, to the lower leg (not shown) of a patient. The distal joint 40 is constructed like the proximal joint 24 and likewise represents a scissor-type rotary joint.

The quarter shells 26.1, 26.2 and 42.1, 42.2 are made of a flexible material, such that they can be adapted to the shape of the respective limb on which they are to be secured. The panels 16.1, 16.2, 18.1, 18.2 are produced as injection-molded plastic parts, for example.

Figure 2:
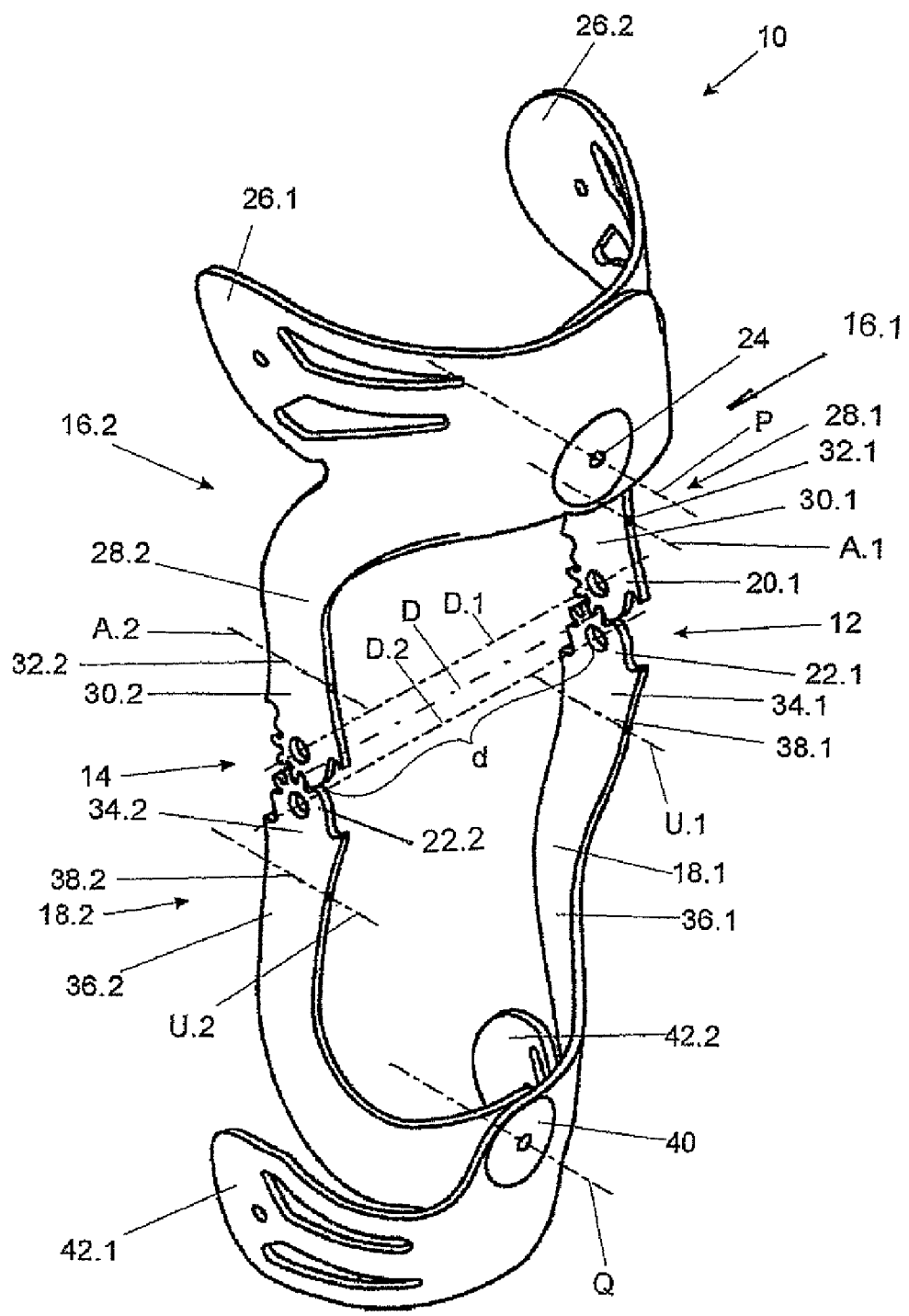
FIG. 2 shows an alternative embodiment of a knee orthosis according to the invention, in which the proximal joint is designed as a rotary joint, but not as a scissor-type rotary joint.

FIG. 2 shows an alternative embodiment of a knee orthosis 10 according to the invention, in which identical reference signs designate identical components. In contrast to the knee orthosis 10 according to FIG. 1, the proximal joint 24 is designed as a rotary joint, but not as a scissor-type rotary joint. Therefore, when the distance d between the left-hand load-bearing joint 12 and the right-hand load-bearing joint 14 decreases, the distance between the two quarter shells 26.1 and 26.2 increases. According to further embodiments of the invention, the distal joint 40 can also be designed like the proximal joint 24 according to FIG. 2.

To adapt the knee orthosis 10, the proximal joint 24 and the distal joint 40, which are both designed as fixable rotary joints, are loosened, and the angle between the proximal panels 16.1, 16.2 and the distal panels 18.1, 18.2 is adjusted such that the distance d between the load-bearing joints 12 and 14 has the desired size. The proximal joint 24 and the distal joint 40 are then fixed, and the knee orthosis 10 is secured to the thigh and lower leg of the patient.

Figure 3:
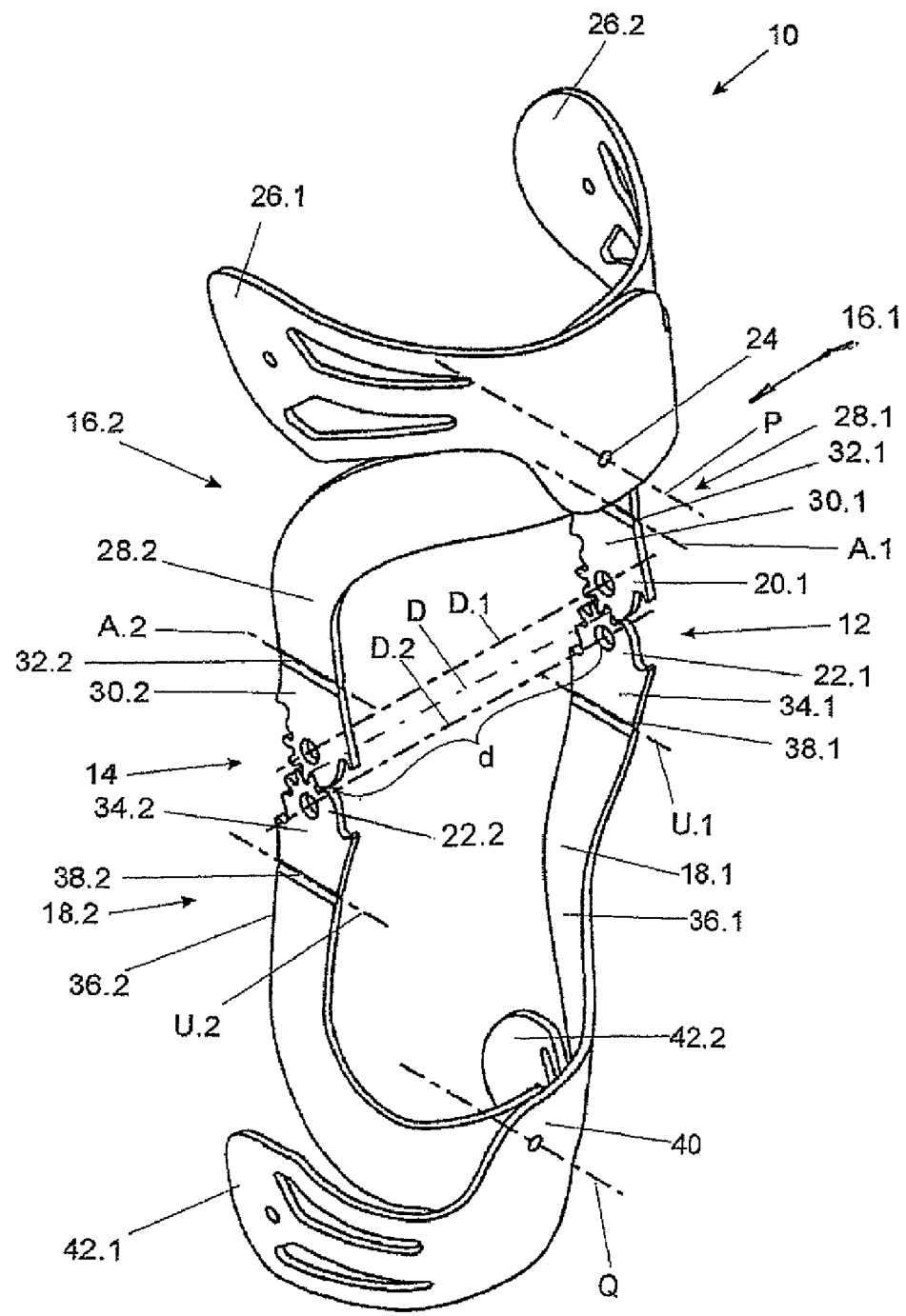
FIG. 3 shows an alternative embodiment of a knee orthosis according to the invention, in which both the proximal joint and also the distal joint are designed as scissor-type rotary joints.

FIG. 3 shows an alternative embodiment of a knee orthosis 10 according to the invention, in which identical reference signs designate identical components. In contrast with the knee orthosis 10 according to FIG. 1, both the proximal joint and also the distal joint are designed as scissor-type rotary joints.

Figure 4:
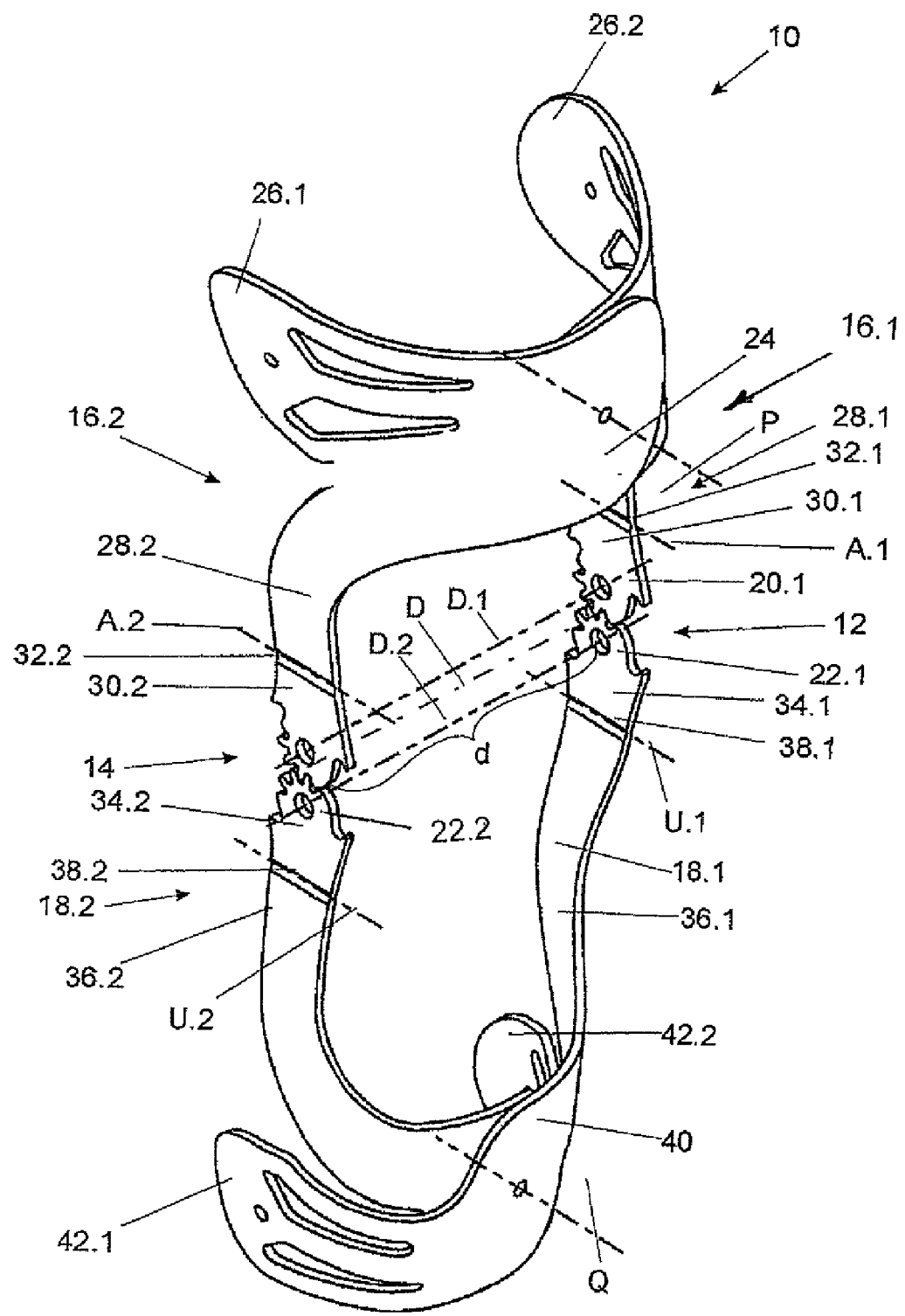
FIG. 4 shows an alternative embodiment of a knee orthosis according to the invention, in which the proximal joint is designed as a rotary joint, but not as a scissor-type rotary joint.

FIG. 4 shows an alternative embodiment of a knee orthosis 10 according to the invention, in which both the proximal joint 24 and also the distal joint 40 are designed as scissor-type rotary joints. The proximal compensating joints 32.1, 32.2 and the distal compensating joints 38.1, 38.2 are formed by tapering of material and can therefore also be designated as monolithic joints.

Figure 5:
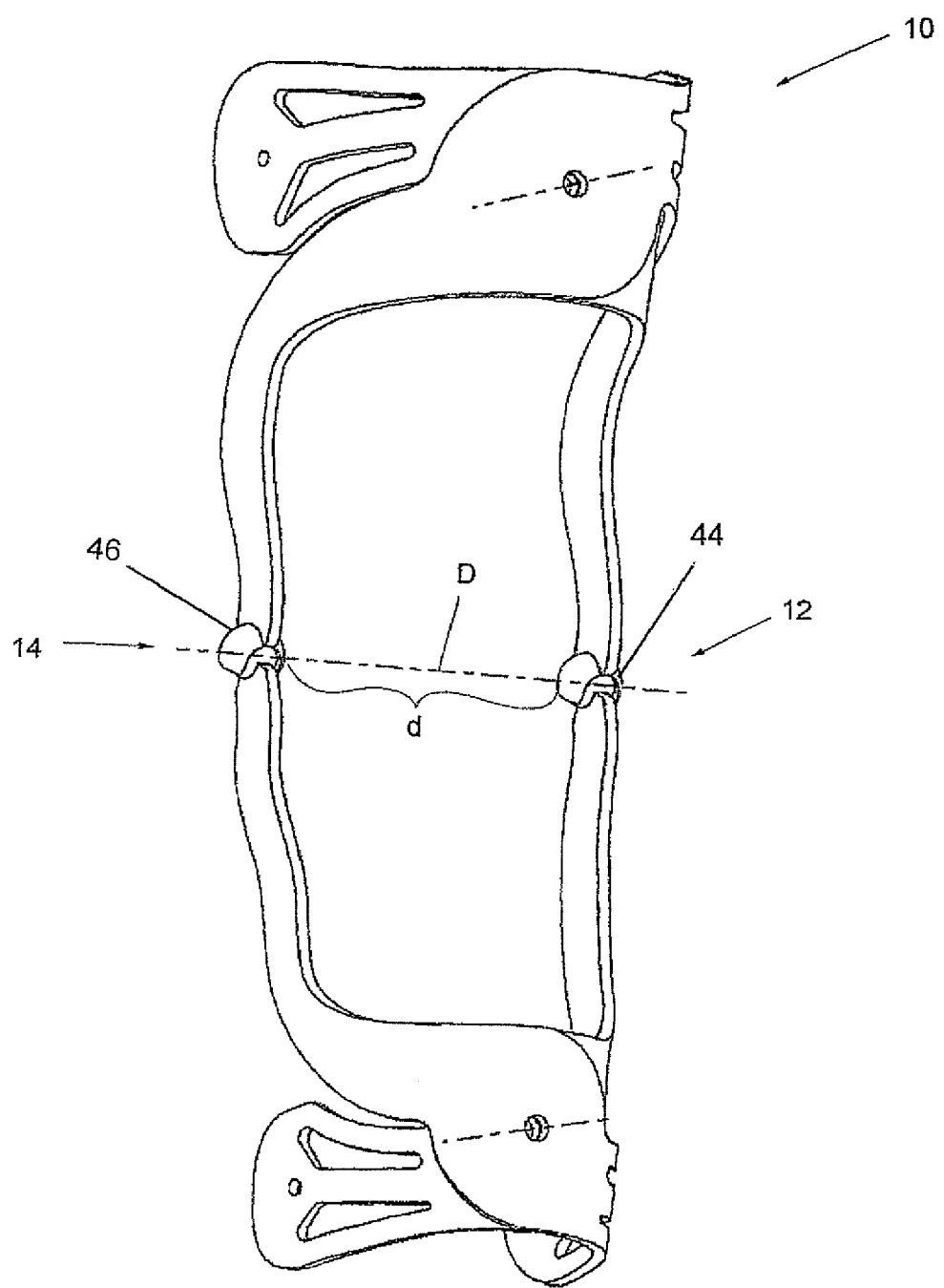
FIG. 5 shows another alternative embodiment of a knee orthosis according to the invention, in which the load-bearing joint is designed as a spherical joint.

FIG. 5 shows an alternative embodiment of a knee orthosis 10 according to the invention, in which the load-bearing joints 12, 14 are designed as spherical joints 44 and 46, respectively, and in which compensating joints can therefore be omitted. Pads (not shown) are secured on the spherical joints in order to ensure that the knee orthosis 10 fits comfortably on the patient's body.

The invention claimed is:

1. An orthosis, with two load-bearing joints (12, 14) that each have a proximal panel (16.1, 16.2) and a distal panel (18.1, 18.2), characterized in that
    (a) the proximal panels (16.1, 16.2) are connected to each other by means of a proximal joint (24), and the distal panels (18.1, 18.2) are connected to each other by means of a distal joint,
    (b) and the proximal panels (16.1, 16.2) are connected, at the proximal joint (24) in the form of a rotary joint, in such a way that they can pivot about a proximal joint pivot axis (P) and can be fixed relative to each other, the proximal joint pivot axis (P) extends through the proximal joint (24) and the proximal joint (24) and/or the distal joint (40) is pivotable about a rotary joint pivot axis (P, Q) that extends perpendicular to a load-bearing joint pivot axis about which the two load-bearing joints (12, 14) are pivotable,
    wherein the two distal panels (18.1, 18.2)
    (c) each have a first distal panel part (34.1, 34.2) and a second distal panel part (36.1, 36.2), and
    (d) each comprise a distal compensating joint (38.1, 38.2), which distal compensating joints (38.1, 38.2) connect the respective panel parts (34.1, 34.2, 36.1, 36.2) to each other pivotably about a pivot axis (U.1, U.2) that extends parallel to the rotary joint pivot axis (Q).

2. The orthosis as claimed in claim 1, characterized in that the proximal joint (24) and/or the distal joint (40) is a scissor-type rotary joint.

3. The orthosis as claimed in claim 2, characterized in that the scissor-type rotary joint is a fixable scissor-type rotary joint.

4. The orthosis as claimed in claim 1, characterized in that the two proximal panels (16.1, 16.2)
    (a) each have a first panel part (28.1, 28.2) and a second panel part (30.1, 30.2), and
    (b) each comprise a proximal compensating joint (32.1, 32.2),
        which proximal compensating joints (32.1, 32.2) connect the respective panel parts (28.1, 28.2, 30.1, 30.2) to each other pivotably about a pivot axis (A.1, A.2) that extends parallel to the rotary joint pivot axis (P).

5. The orthosis as claimed in claim 1, characterized in that the compensating joints (32.1, 32.2, 38.1, 38.2) are hinge joints.

6. The orthosis as claimed in claim 1, characterized in that the compensating joints (32.1, 32.2, 38.1, 38.2) are formed by tapering of the material of the respective panels (16.1, 16.2, 18.1, 18.2) and/or by materials with different strength characteristics.

7. An orthosis with two load-bearing joints (12, 14) that each have a proximal panel (16.1, 16.2) and a distal panel (18.1, 18.2), characterized in that
    (a) the proximal panels (16.1, 16.2) are connected to each other by means of a proximal joint (24), and the distal panels (18.1, 18.2) are connected to each other by means of a distal joint (40),
    (b) and the proximal panels (16.1, 16.2) are connected, at the proximal joint (24) in the form of a rotary joint, in such a way that they can pivot about a proximal joint pivot axis (P) and can be fixed relative to each other, wherein the proximal panels (16.1, 16.2), seen from the direction of the respective load-bearing joint (12, 14), run out behind the proximal joint (24) into a quarter shell (26.1, 26.2), such that both quarter shells form a proximal half shell for securing the orthosis (10) to a limb of the body.

8. The orthosis as claimed in claim 7, characterized in that the proximal quarter shells (26.1, 26.2) and/or the distal quarter shells (42.1, 42.2) are flexible in order to permit adaptation to the limb of the body.

9. The orthosis as claimed in claim 7, characterized in that it is a frame-type knee orthosis.

10. The orthosis as claimed in claim 7, characterized in that the load-bearing joints are monocentric.

11. The orthosis as claimed in claim 7, characterized in that the load-bearing joints are polycentric.

12. The orthosis as claimed in claim 7, characterized in that it is an elbow orthosis.

13. The orthosis as claimed in claim 7, characterized in that the load-bearing joints (12, 14) are spherical joints.

14. An orthosis with two load-bearing joints (12, 14) that each have a proximal panel (16.1, 16.2) and a distal panel (18.1, 18.2), characterized in that
    (a) the proximal panels (16.1, 16.2) are connected to each other by means of a proximal joint (24), and the distal panels (18.1, 18.2) are connected to each other by means of a distal joint (40),
    (b) and the proximal panels (16.1, 16.2) are connected, at the proximal joint (24) in the form of a rotary joint, in such a way that they can pivot about a proximal joint pivot axis (P) and can be fixed relative to each other, wherein the distal panels (18.1, 18.2), seen from the direction of the respective load-bearing joint (12, 14), run out behind the distal joint (40) into a quarter shell (42.1, 42.2), such that both quarter shells (42.1, 42.2) form a distal half shell for securing the orthosis (10) to a limb of the body.

15. The orthosis as claimed in claim 14, characterized in that it is a frame-type knee orthosis.

16. The orthosis as claimed in claim 14, characterized in that the load-bearing joints are monocentric.

17. The orthosis as claimed in claim 14, characterized in that the load-bearing joints are polycentric.

18. The orthosis as claimed in claim 14, characterized in that it is an elbow orthosis.

19. The orthosis as claimed in claim 14, characterized in that the load-bearing joints (12, 14) are spherical joints.

* * * * *